US010406020B2

(12) United States Patent
Kang

(10) Patent No.: US 10,406,020 B2
(45) Date of Patent: Sep. 10, 2019

(54) HYPERHIDROSIS TREATMENT APPARATUS

(71) Applicant: Sun-young Kang, Seoul (KR)

(72) Inventor: Sun-young Kang, Seoul (KR)

( * ) Notice: Subject to any disclaimer, the term of this patent is extended or adjusted under 35 U.S.C. 154(b) by 742 days.

(21) Appl. No.: 15/090,626

(22) Filed: Apr. 5, 2016

(65) Prior Publication Data

US 2017/0027742 A1    Feb. 2, 2017

(30) Foreign Application Priority Data

Jul. 31, 2015   (KR) .................. 10-2015-0108998

(51) Int. Cl.
*A61F 7/00* (2006.01)

(52) U.S. Cl.
CPC ...... *A61F 7/007* (2013.01); *A61F 2007/0052* (2013.01); *A61F 2007/0076* (2013.01); *A61F 2007/0087* (2013.01)

(58) Field of Classification Search
None
See application file for complete search history.

(56) References Cited

U.S. PATENT DOCUMENTS

| | | | | |
|---|---|---|---|---|
| 6,045,549 A | * | 4/2000 | Smethers ........... | A61B 18/1477 604/22 |
| 6,558,379 B1 | | 5/2003 | Batchelor et al. .............. | 606/41 |
| 8,021,360 B2 | * | 9/2011 | Dunning ................ | A61B 18/16 606/32 |
| 2002/0019379 A1 | | 2/2002 | Kagan et al. .................. | 514/179 |
| 2002/0120261 A1 | * | 8/2002 | Morris ............... | A61B 18/1477 606/41 |
| 2011/0046615 A1 | * | 2/2011 | Manstein ........... | A61B 18/1477 606/9 |

FOREIGN PATENT DOCUMENTS

| | | |
|---|---|---|
| KR | 10-1073839 B1 | 10/2011 |
| KR | 10-1076698 B1 | 10/2011 |
| KR | 10-1133947 B1 | 4/2012 |
| KR | 101158009 B1 * | 6/2012 |
| KR | 101394214 B1 * | 5/2014 |
| KR | 10-1456230 B1 | 11/2014 |

OTHER PUBLICATIONS

Korean to English Translation of KR-101158009-B1 (Year: 2012).*
Korean to English Translation of KR-101394214-B1 (Year: 2014).*

* cited by examiner

*Primary Examiner* — Ronald Hupczey, Jr.
*Assistant Examiner* — Dustin P Clary
(74) *Attorney, Agent, or Firm* — Stein IP, LLC

(57) ABSTRACT

Disclosed is a hyperhidrosis treatment apparatus including a contact part which is detachably mounted and gets in contact with a user's skin so that the contact part can be easily replaced with a new one.

5 Claims, 6 Drawing Sheets

HYPERHIDROSIS TREATMENT APPARATUS

BACKGROUND OF THE INVENTION

Field of the Invention

The present invention relates to a hyperhidrosis treatment apparatus, and more particularly, to a hyperhidrosis treatment apparatus including a contact part which is detachably mounted and gets in contact with a user's skin so that the contact part can be easily replaced with a new one.

Background Art

In general, as widely known, a hyperhidrosis treatment apparatus destroys sweat glands by applying electric currents to a probe which gets in contact with a user's skin.

In other words, a probe penetrates into sweat glands (eccrine glands) concerned with excessive sweating or sweat glands (apocrine glands) causing osmidrosis and applies high-frequency stimulation in order to destroy the sweat glands by thermal action. Then, hyperhidrosis can be treated. FIG. 1 illustrates a hyperhidrosis treatment apparatus disclosed in Korean Patent No. 10-1456230. Referring to FIG. 1, the hyperhidrosis treatment apparatus according to a prior art will be described.

As shown in the drawing, the hyperhidrosis treatment apparatus includes: a probe P which gets in contact with a user's skin; a contact part 13 which is mounted at one side of the probe P and of which one side gets in contact with the user's skin and the other side gets in contact with a thermoelectric element; and an upper case 11 and a lower case 12 to which the contact part 13 is mounted.

That is, the probe P penetrates into the human skin tissue and applies high-frequency stimulation. The probe P passes through a through hole of a skin contact part 13-1 of the contact part 13 and is attached to the human skin tissue.

In the meantime, in order to control temperature of the contact part 13, a cooling contact part 13-2 of the contact part 13 gets in contact with the thermoelectric element.

Through the above structure, the hyperhidrosis treatment apparatus according to the prior art can treat hyperhidrosis, but has the following disadvantages.

In other words, because the contact part 13 is arranged between the upper case 11 and the lower case 12 as shown in the drawing, in order to replace the contact part 13 with a new one, the upper case 11 and the lower case 12 are separated from each other, and then, reassembled after the contact part 13 is replaced with a new one. Therefore, the conventional hyperhidrosis treatment apparatus has a disadvantage in that it is difficult to replace the contact part 13 with a new one when the contact part's life ends or the contact part is damaged.

Meanwhile, because technologies for the hyperhidrosis treatment apparatus have been widely used and described in the following cited references in detail, description and illustration thereof will be omitted.

CITED REFERENCES

Cited Reference 1: U.S. patent Ser. No. 06/558,379
Cited Reference 2: U. S. Patent Publication No. 2002019379
Cited Reference 3: Korean Patent No. 10-1073839
Cited Reference 4: Korean Patent No. 10-1133947
Cited Reference 5: Korean Patent No. 10-1076698
Cited Reference 6: Korean Patent No. 10-1456230

SUMMARY OF THE INVENTION

Accordingly, the present invention has been made in view of the above-mentioned problems occurring in the prior art, and it is an object of the present invention to provide a hyperhidrosis treatment apparatus which has a contact part detachably mounted so that the contact part can be easily replaced with a new one.

To accomplish the above object, according to the present invention, there is provided a hyperhidrosis treatment apparatus including: a probe which gets in contact with a user's skin, a contact part which is mounted at one side of the probe and of which one side gets in contact with the user's skin and the other side gets in contact with a thermoelectric element, and an upper case and a lower case to which the contact part is mounted, wherein the contact part includes: a cooling contact part which gets in contact with the thermoelectric element; and a skin contact part which gets in contact with the user's skin and is bent at a predetermined angle so that the probe penetrates therethrough and the cooling contact part and the skin contact part are joined to each other in a detachable manner.

Moreover, the cooling contact part is formed in a plate type, and includes: a first main body which gets in contact with the thermoelectric element; a flat part which is formed at one side of the first main body and is thinner than the first main body and whose bottom side extends to the first main body uniformly; and a joining part which protrudes on the flat part, is lower than the first main body and is dented relative to the direction that the skin contact part is joined. The skin contact part includes: a second main body bent at a predetermined angle, the second main body having one side joined with the cooling contact part and the other side through which the probe penetrates; a flat part which is formed at one side of the second main body and is thinner than the second main body and whose upper side extends uniformly; and an insertion protrusion part which protrudes on the bottom side of the flat part toward the cooling contact part and is lower than the second main body.

Furthermore, the insertion protrusion part of the second main body comes into contact with the flat part of the first main body and is inserted into a dented portion of the joining part, the bottom side of the flat part of the second main body abuts on the upper side of the joining part of the first main body, and the flat part of the first main body and the flat part of the second main body have the same length, so that the cooling contact part and the skin contact part come into close contact with each other when the first main body is joined to the second main body.

Additionally, the hyperhidrosis treatment apparatus further includes a pressing part which is arranged at one side of the lower case to press the contact part toward the lower case, and the pressing part includes: a roller part which presses a part of the contact part to which the first main body and the second main body are joined; and a support part on which the roller part is rotatably mounted.

In addition, the support part includes: a support part main body of a plate type; and vertical parts which are formed in the vertical direction to one side of the support part main body and have a pair of plate bodies spaced apart from each other at a predetermined interval, and the roller part includes: a rotating pin which is rotatably mounted between the vertical parts; and a roller which is mounted on the rotating pin. An elastic pressing part is mounted on the outer surface of the roller in order to press the joined portion between the first main body and the second main body.

Furthermore, the lower case includes: a first fixing pole which is mounted at one side of the lower case to abut on the side of the support part main body; and a second fixing pole which is mounted on the bottom side of the support part main body. The first fixing pole is inserted into a groove part formed at one side of the support part main body, and a fixture is inserted into the second fixing pole through a through hole formed in the support part main body.

Additional features and advantages of the present invention will be shown in the following description, will be apparent by the following description, and will be known well through practice of the present invention.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention basing upon the principle that an inventor can properly define the concepts of words in order to describe his or her own invention in the best way.

The hyperhidrosis treatment apparatus according to the preferred embodiment of the present invention enables the user to easily replace the contact part with a new one.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Further, the terms as will be discussed later are defined in accordance with the functions of the present invention, but may be varied under the intention or regulation of a user or operator. Therefore, they should be defined on the basis of the whole scope of the present invention.

Moreover, it will be understood by those of ordinary skill in the art that the following embodiment of the present invention does not limit the technical scope of the present invention and is just exemplified. It will be also understood that all changes, modifications and equivalents may be made therein without departing from the technical idea and scope of the present invention and belong to the technical scope of the present invention.

Figure 1:
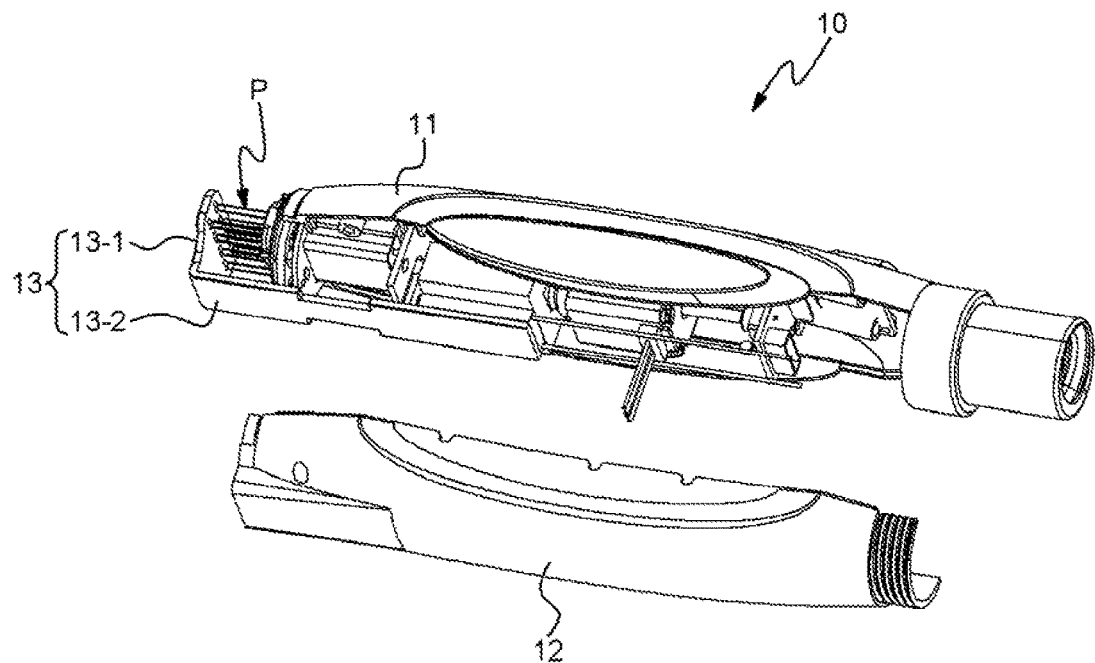
FIG. 1 is a perspective view showing a hyperhidrosis treatment apparatus according to a prior art.
Figure 2:
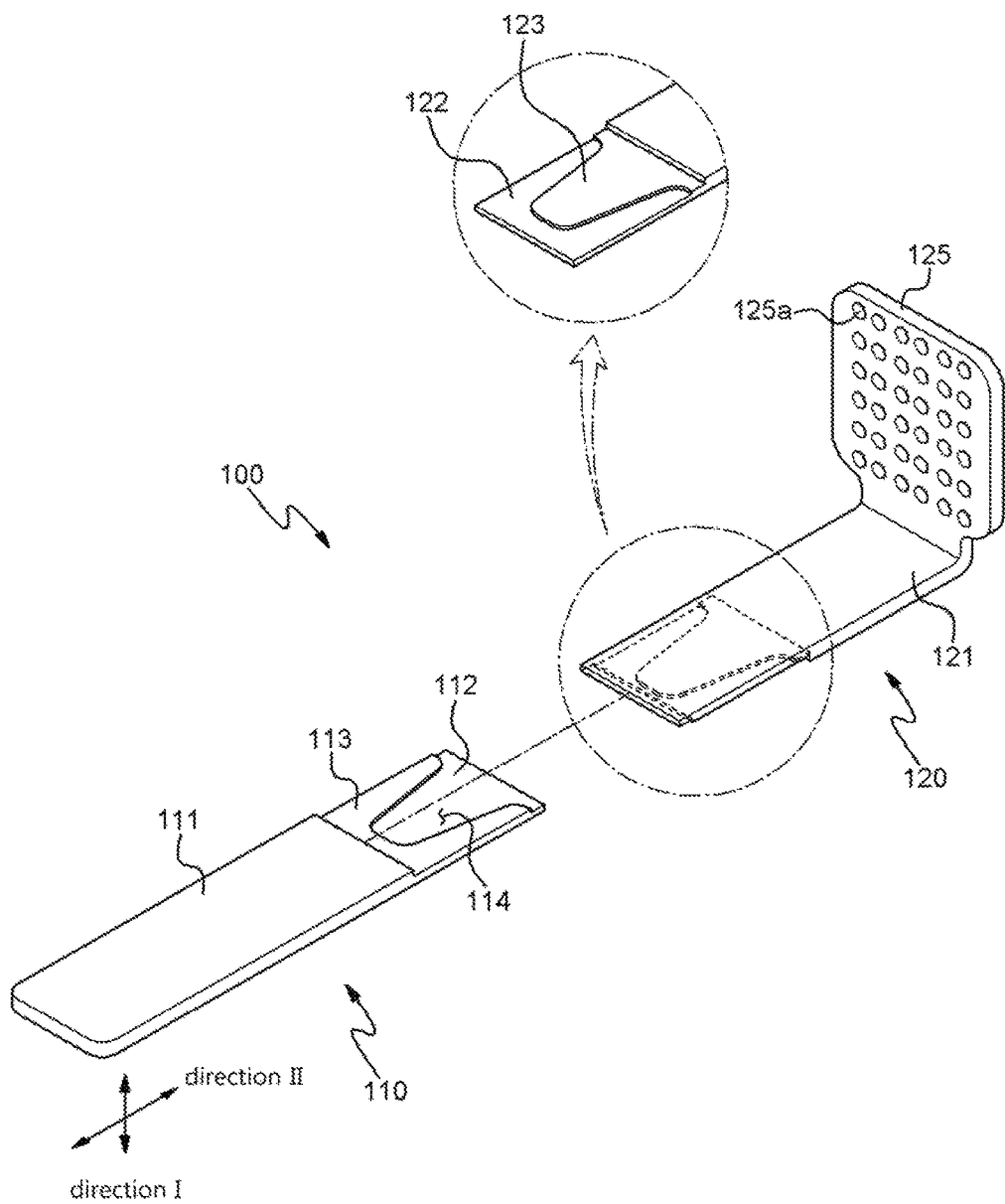
FIG. 2 is a perspective view of a contact part of a hyperhidrosis treatment apparatus according to a preferred embodiment of the present invention, wherein a part of a second main body is enlargedly illustrated upside down.
Figure 3:
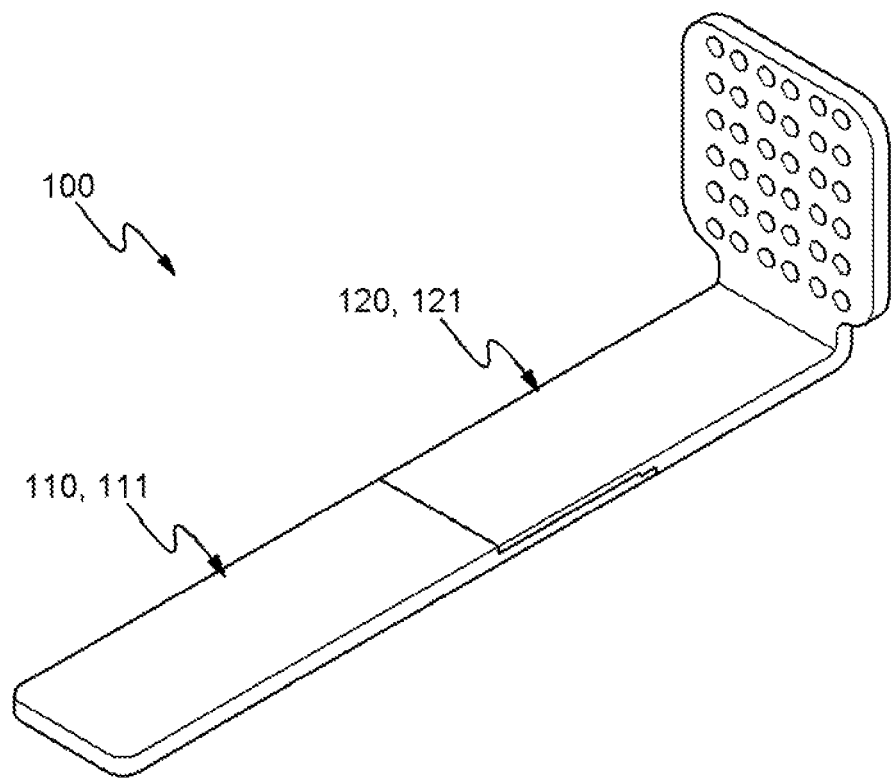
FIG. 3 is a perspective view showing a state where the contact part of the hyperhidrosis treatment apparatus is joined.
Figure 4:
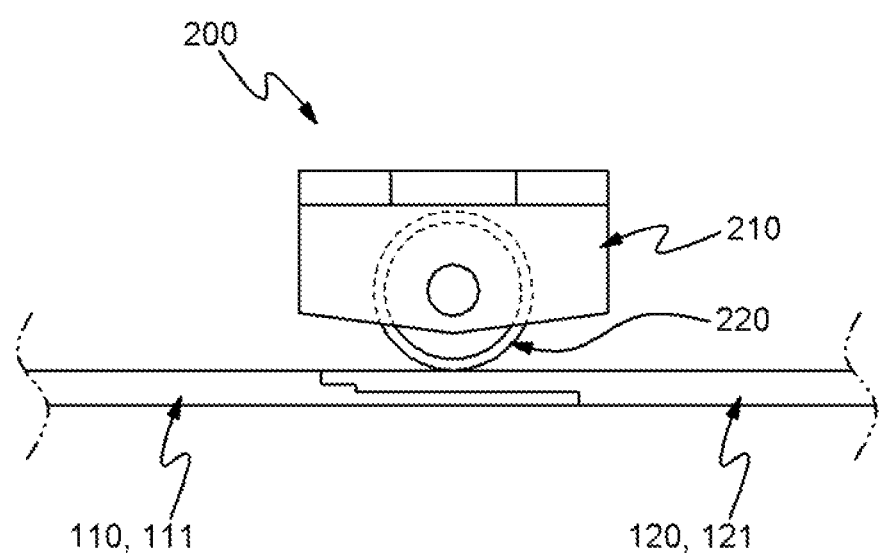
FIG. 4 is a schematic diagram showing a state where a pressing part comes into contact with the contact part of the hyperhidrosis treatment apparatus.
Figure 5:
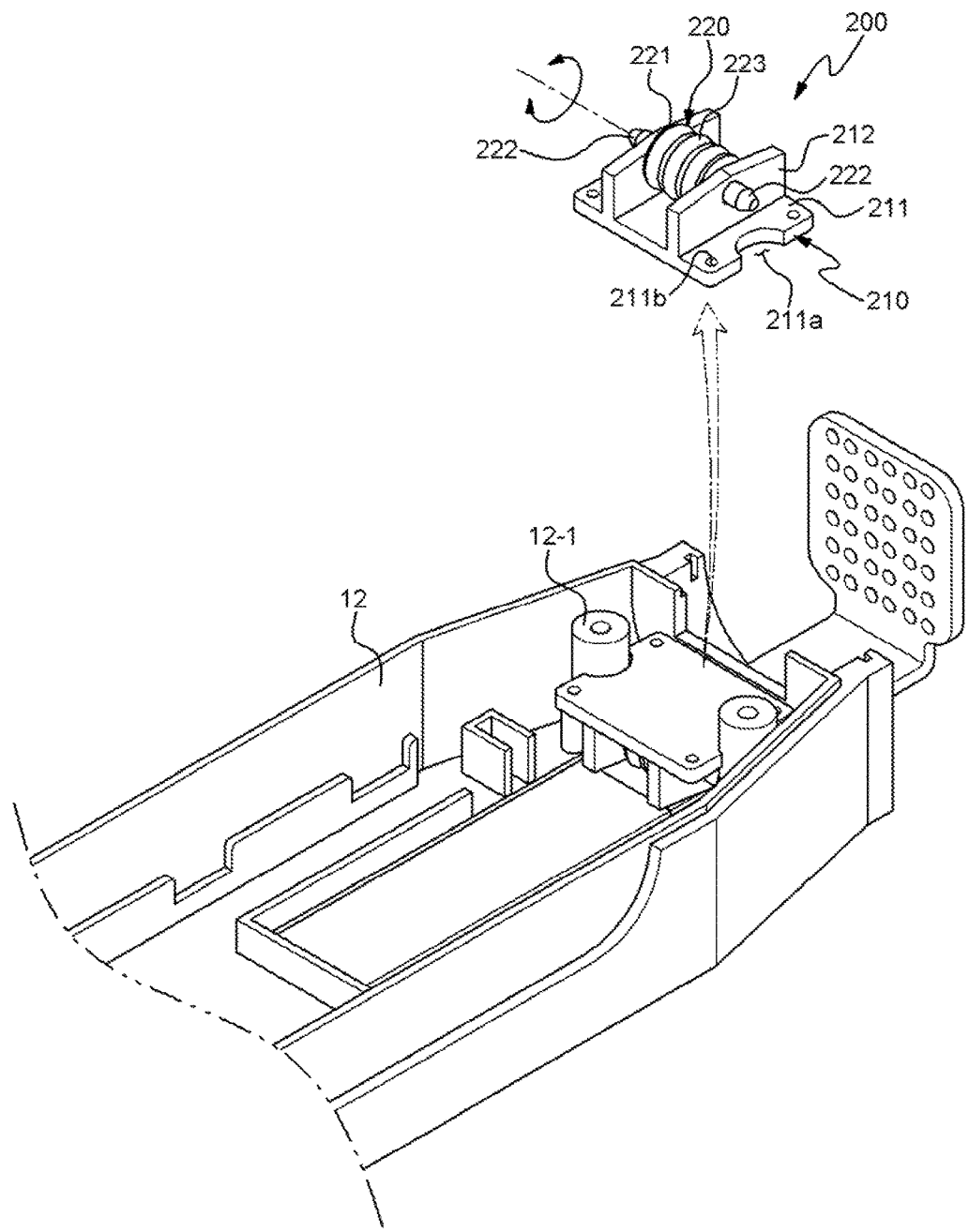
FIG. 5 is a perspective view showing a state where the pressing part of the hyperhidrosis treatment apparatus is mounted.
Figure 6:
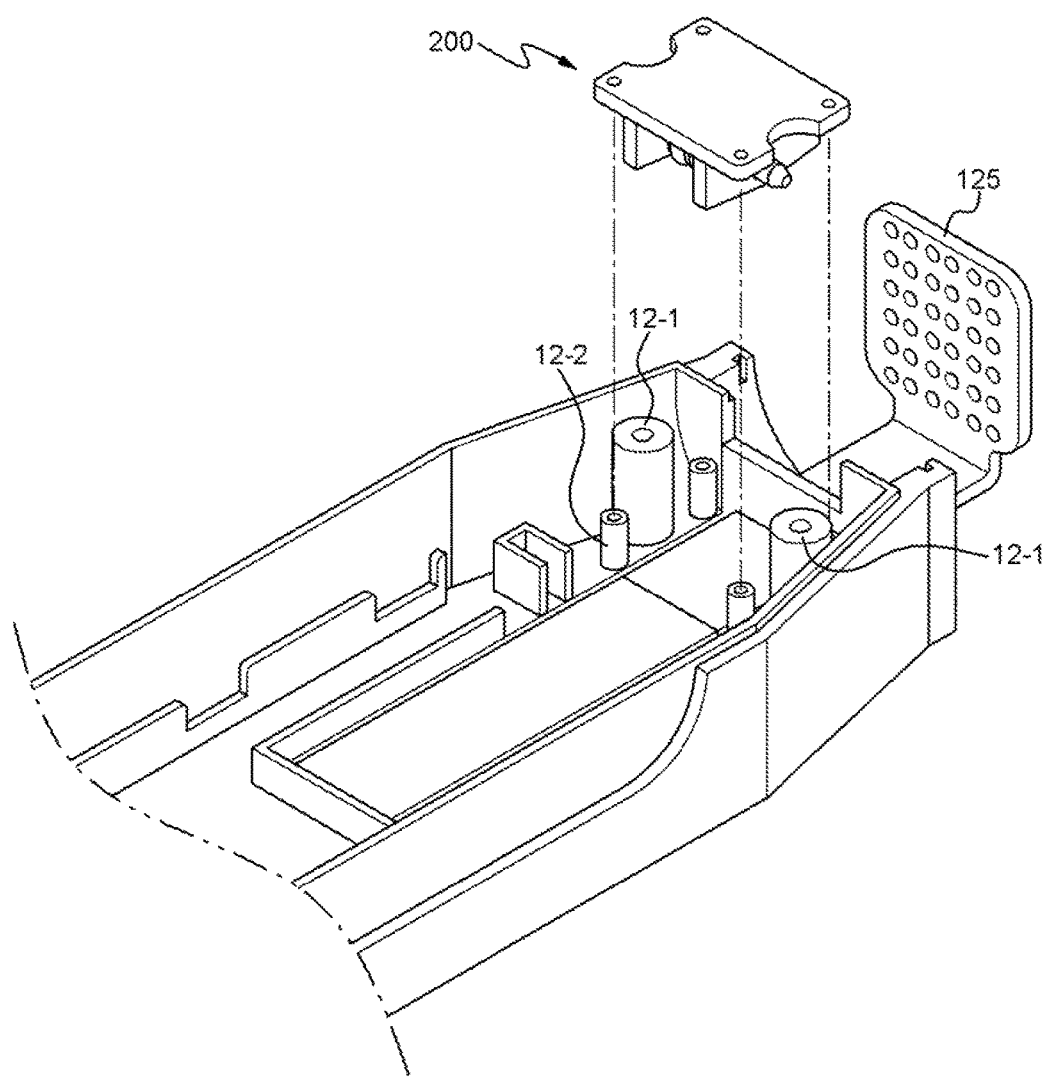
FIG. 6 is a perspective view showing a state where the pressing part of the hyperhidrosis treatment apparatus is detached.

FIG. 2 is a perspective view of a contact part of a hyperhidrosis treatment apparatus according to a preferred embodiment of the present invention, wherein a part of a second main body is enlargedly illustrated upside down, FIG. 3 is a perspective view showing a state where the contact part of the hyperhidrosis treatment apparatus is joined, FIG. 4 is a schematic diagram showing a state where a pressing part comes into contact with the contact part of the hyperhidrosis treatment apparatus, FIG. 5 is a perspective view showing a state where the pressing part of the hyperhidrosis treatment apparatus is mounted, and FIG. 6 is a perspective view showing a state where the pressing part of the hyperhidrosis treatment apparatus is detached.

EMBODIMENT

As shown in FIGS. 2 and 3, the hyperhidrosis treatment apparatus 10 according to the preferred embodiment of the present invention includes: a probe P which gets in contact with a user's skin; a contact part 100 which is mounted at one side of the probe P and of which one side gets in contact with the user's skin and the other side gets in contact with a thermoelectric element; and an upper case 11 and a lower case 12 to which the contact part 100 is mounted.

In this instance, the contact part 100 includes: a cooling contact part 110 which gets in contact with the thermoelectric element; and a skin contact part 120 which gets in contact with the user's skin and is bent at a predetermined angle so that the probe P penetrates therethrough. The cooling contact part 110 and the skin contact part 120 are joined to each other in a detachable manner.

In other words, because the cooling contact part 110 and the skin contact part 120 are joined to each other in a detachable manner, when the user wants to replace the skin contact part 120 with a new one, the skin contact part 120 can be replaced with a new one by being detached from the cooling contact part 110. Therefore, the hyperhidrosis treatment apparatus according to the present invention is easier in replacement of the skin contact part than the hyperhidrosis treatment apparatuses according to the prior arts.

In the meantime, there are various configurations in order to detachably mount the cooling contact part 110 and the skin contact part 120, but as shown in the drawing, it is possible that the cooling contact part 110 and the skin contact part 120 are joined to each other by male-and-female coupling.

For this, the cooling contact part 110 is formed in a plate type, and includes: a first main body 111 which gets in contact with the thermoelectric element; a flat part 112 which is formed at one side of the first main body 111 and is thinner than the first main body 111 and whose bottom side extends to the first main body 111 uniformly; and a joining part 113 which protrudes on the flat part 112, is lower than the first main body 111 and is dented relative to the direction that the skin contact part 120 is joined.

That is, as shown in the drawing, the flat part 112 may formed in a stepped shape because it is thinner than the first main body 111, and the joining part 113 protrudes on the flat part 112 in the height direction (in the direction I). In this instance, as shown in the drawing, the joining part 113 is dented based on the direction that the skin contact art 120 is joined (in the direction II).

In other words, the joining part 113 has a dented portion 114 which is dented in the left direction in the drawing.

Meanwhile, the skin contact part 120 includes: a second main body 121 bent at a predetermined angle, the second main body 121 having one side joined with the cooling contact part 110 and the other side through which the probe P penetrates; a flat part 122 which is formed at one side of the second main body 121 and is thinner than the second main body 121 and whose upper side extends uniformly; and an insertion protrusion part 123 which protrudes on the bottom side of the flat part 122 toward the cooling contact part 110 and is lower than the second main body 121.

That is, the flat part 122 is formed on the bottom side of the second main body 121. As shown in the drawing, the bottom side of the flat part 122 is formed in a stepped shape because the flat part 122 is thinner than the second main body 121. In this instance, the insertion protrusion part 123 protrudes on the bottom side in the direction of the cooling contact part 110 (in the direction II).

Such an insertion protrusion part 123 is inserted into the dented portion 114.

That is, the insertion protrusion part 123 of the second main body 121 comes into contact with the flat part 112 of the first main body 111 and is inserted into the dented portion 114 of the joining part 113.

In this instance, the bottom side of the flat part 122 of the second main body 121 abuts on the upper side of the joining part 113 of the first main body 111, and the flat part 112 of the first main body 111 and the flat part 122 of the second main body 121 have the same length, so that the cooling contact part 110 and the skin contact part 120 come into close contact with each other when the first main body 111 is joined to the second main body 121.

In other words, the left side of the flat part 122 of the second main body 121 gets in contact with a stepped jaw between the first main body 111 and the flat part 112, and the right side of the flat part 112 of the first main body 111 gets in contact with a stepped jaw between the second main body 121 and the flat part 122.

As shown in FIG. 3, when the first main body 111 and the second main body 121 are joined with each other, the cooling contact part 110 and the skin contact part 120 come into close contact with each other.

In the meantime, in FIG. 2, as described above, the flat part 122 and the insertion protrusion part 123 of the skin contact part 120 are formed on the bottom side of the second main body 121, and the enlarged part in the FIG. 2 shows an upside down state of the flat part 122 and the insertion protrusion part 123 of the skin contact part 120 in order to clearly show them.

As described above, because the contact part 100 of the present invention includes the cooling contact part 110 and the skin contact part 120 which are detachably attached to each other, the hyperhidrosis treatment apparatus according to the present invention enables the user to easily replace the contact part with a new one.

In FIG. 2 the reference numeral 125 designates a pin penetrating part, and pins P are exposed to the outside by penetrating through holes 125a, and because it is the same as that of the prior arts, repeated description will be omitted.

In the meantime, as described above, because the cooling contact part 110 and the skin contact part 120 are joined with each other by the male-and-female coupling, the cooling contact part 110 and the skin contact part 120 are fixed stably.

For this, as shown in FIGS. 4 to 6, the hyperhidrosis treatment apparatus includes a pressing part 200 which is arranged at one side of the lower case 12 to press the contact part 100 toward the lower case 12.

That is, the contact part 100 is fixed more stably because being pressed by the pressing part 200.

For this, the pressing part 200 includes: a roller part 220 which presses a part of the contact part 100 to which the first main body 111 and the second main body 121 are joined; and a support part 210 on which the roller part 220 is rotatably mounted.

In other words, the roller part 220 presses the joined portion between the first main body 111 and the second main body 121 so that the first main body 111 and the second main body 121 are fixed stably, and the roller part 220 is rotatably mounted on the support part 210, so that the second main body 121 can be easily drawn out because the roller part 220 rotates when the second main body 121 is drawn out.

Meanwhile, as shown in the drawing, the support part 210 includes: a support part main body 211 of a plate type; and vertical parts 212 which are formed in the vertical direction to one side of the support part main body 211 and have a pair of plate bodies spaced apart from each other at a predetermined interval.

Furthermore, the roller part 220 includes: a rotating pin 222 which is rotatably mounted between the vertical parts 212; and a roller 221 which is mounted on the rotating pin 222.

Namely, because the roller 221 is mounted on the rotating pin 222 and the rotating pin 222 is rotatably mounted between the vertical parts 212, the second main body 121 can be easily drawn out while the roller 221 rotates when the second main body 121 is drawn out.

In this instance, the rotating pin 222 is inserted into through holes of the vertical parts 212. In this instance, in order to mount the rotating pin 222 to be able to rotate, the diameter of the rotating pin 222 may be smaller than the through holes or a bearing may be mounted on the through holes, however, detailed descriptions of such technologies will be omitted because they have been known widely.

In the meantime, it is possible that an elastic pressing part 223 made with rubber or other materials is mounted on the outer surface of the roller 221 in order to press the joined portion between the first main body 111 and the second main body 121.

As described above, the roller 221 presses the joined portion between the first main body 111 and the second main body 121, and in this instance, if the elastic pressing part 223 presses the joined portion, the joined portion can be pressed in a safer way without any damage.

Additionally, in order to fix the pressing part 200 more stably, the lower case 12 includes: a first fixing pole 12-1 which is mounted at one side of the lower case 12 to abut on the side of the support part main body 211; and a second fixing pole 12-2 which is mounted on the bottom side of the support part main body 211.

In this instance, the first fixing pole 12-1 is inserted into a groove part 211a formed at one side of the support part main body 211, and a fixture (not shown) is inserted into the second fixing pole 12-2 through a through hole 211b formed in the support part main body 211.

While the present invention has been particularly shown and described with reference to the embodiment thereof, it will be understood by those of ordinary skill in the art that the present invention is not restricted to the embodiment and various changes, modification and equivalences may be made therein within the technical scope of the present invention.

It will be also understood that all changes and modifications of the present invention belong to the scope of the present invention and the protective scope of the present invention will be clarified by the following claims.

What is claimed is:

1. A hyperhidrosis treatment apparatus including a probe configured to contact a user's skin, a contact part which is mounted at one side of the probe and of which one side is configured to contact the user's skin and the other side is configured to contact a thermoelectric element, and an upper case and a lower case to which the contact part is mounted,
wherein the contact part includes: a cooling contact part configured to contact the thermoelectric element; and a skin contact part configured to contact the user's skin and is bent at a predetermined angle so that the probe penetrates therethrough, and
wherein the cooling contact part and the skin contact part are joined to each other in a detachable manner,
wherein the cooling contact part is of a plate type, and includes: a first main body configured to contact the thermoelectric element; a flat part configured to be attached to the first main body and is thinner than the first main body and whose bottom side extends to the first main body uniformly; and a joining part which protrudes on the flat part, is lower than the first main body and is dented relative to the direction that the skin contact part is joined, and
wherein the skin contact part includes: a second main body bent at a predetermined angle, the second main body having one side joined with the cooling contact part and the other side through which the probe penetrates; a flat part configured to be attached to the second main body and is thinner than the second main body and whose upper side extends uniformly; and an insertion protrusion part which protrudes on the bottom side of the flat part toward the cooling contact part and is lower than the second main body.

2. The hyperhidrosis treatment apparatus according to claim 1, wherein the insertion protrusion part of the second main body is configured to contact the flat part of the first main body and is inserted into a dented portion of the joining part,
wherein the bottom side of the flat part of the second main body abuts on the upper side of the joining part of the first main body, and
wherein the flat part of the first main body and the flat part of the second main body have the same length, so that the cooling contact part and the skin contact part come into close contact with each other when the first main body is joined to the second main body.

3. The hyperhidrosis treatment apparatus according to claim 1, further including a pressing part which is arranged at one side of the lower case to press the contact part toward the lower case,
wherein the pressing part includes: a roller part which presses a part of the contact part to which the first main body and the second main body are joined; and a support part on which the roller part is rotatably mounted.

4. The hyperhidrosis treatment apparatus according to claim 3, wherein the support part includes: a support part main body of a plate type; and vertical parts which are formed in the vertical direction to one side of the support part main body and have a pair of plate bodies spaced apart from each other at a predetermined interval,
wherein the roller part includes: a rotating pin which is rotatably mounted between the vertical parts; and a roller which is mounted on the rotating pin, and
wherein an elastic pressing part is mounted on the outer surface of the roller in order to press the joined portion between the first main body and the second main body.

5. The hyperhidrosis treatment apparatus according to claim 3, wherein the lower case includes: a first fixing pole which is mounted at one side of the lower case to abut on the side of the support part main body; and a second fixing pole which is mounted on the bottom side of the support part main body, and
wherein the first fixing pole is inserted into a groove part formed at one side of the support part main body, and a fixture is inserted into the second fixing pole through a through hole formed in the support part main body.

* * * * *